(12) United States Patent
Harari et al.

(10) Patent No.: US 10,687,850 B2
(45) Date of Patent: Jun. 23, 2020

(54) SYSTEM AND METHOD FOR PELVIC FLOOR PROCEDURES

(71) Applicant: FEMSELECT LTD., Modi'in (IL)

(72) Inventors: Boaz Harari, Ganei-Tikva (IL); Eyal Sandach, Yahud (IL)

(73) Assignee: FEMSELECT LTD., Modi'in (IL)

( * ) Notice: Subject to any disclaimer, the term of this patent is extended or adjusted under 35 U.S.C. 154(b) by 161 days.

(21) Appl. No.: 16/036,330

(22) Filed: Jul. 16, 2018

(65) Prior Publication Data

US 2019/0008558 A1   Jan. 10, 2019

Related U.S. Application Data

(63) Continuation of application No. 14/667,954, filed on Mar. 25, 2015, now Pat. No. 10,098,664.

(Continued)

(51) Int. Cl.
*A61B 17/42* (2006.01)
*A61B 17/04* (2006.01)
*A61B 17/34* (2006.01)
*A61B 8/12* (2006.01)
*A61B 8/00* (2006.01)
*A61B 90/00* (2016.01)

(52) U.S. Cl.
CPC .......... *A61B 17/42* (2013.01); *A61B 17/0401* (2013.01); *A61B 17/0482* (2013.01); *A61B 8/12* (2013.01); *A61B 8/42* (2013.01); *A61B 2017/0403* (2013.01); *A61B 2017/0409* (2013.01); *A61B 2017/0412* (2013.01); *A61B 2017/0437* (2013.01); *A61B 2017/0448* (2013.01); *A61B 2017/0464* (2013.01); *A61B 2017/3413* (2013.01); *A61B 2090/08021* (2016.02); *A61B 2090/3925* (2016.02)

(58) Field of Classification Search
CPC ............ A61B 1/00087; A61B 1/00098; A61B 1/0014; A61B 17/42; A61B 2017/4216; A61B 2017/4241; A61B 17/0401; A61B 2017/0409; A61B 2017/0411
See application file for complete search history.

(56) References Cited

U.S. PATENT DOCUMENTS 4,877,033 A   10/1989   Seitz, Jr.
5,220,690 A   6/1993   Hoos
(Continued)

FOREIGN PATENT DOCUMENTS

CA   2093824   10/1994
DE   2910410   12/1979
(Continued)

OTHER PUBLICATIONS

An International Search Report and a Written Opinion both dated Mar. 17, 2017, which issued during the prosecution of Applicant's PCT/IL2016/051338.

(Continued)

*Primary Examiner* — Wade Miles
(74) *Attorney, Agent, or Firm* — Sughrue Mion, PLLC

(57) ABSTRACT

A delivery device for tissue anchor delivery is provided. The delivery device includes a first flexible tube having a rigid distal portion attachable to a tissue anchor, a second flexible tube coaxially disposed around the first tube and a tubular sheath covering the second flexible tube. Also provided is a system which includes an imaging device coupler reversibly attached to the delivery device through guides.

3 Claims, 9 Drawing Sheets

Related U.S. Application Data

(60) Provisional application No. 61/989,623, filed on May 7, 2014.

(56) References Cited

U.S. PATENT DOCUMENTS

| | | | |
|---|---|---|---|
| 6,066,104 | A | 5/2000 | Dao et al. |
| 6,332,888 | B1 | 12/2001 | Levy et al. |
| 6,355,017 | B2 | 3/2002 | Buttgen et al. |
| 6,506,190 | B1 | 1/2003 | Walshe |
| 6,602,251 | B2 | 8/2003 | Burbank et al. |
| 7,393,319 | B2 | 7/2008 | Merade et al. |
| 8,257,366 | B2 | 9/2012 | Schneider et al. |
| 8,535,216 | B2 | 9/2013 | Chu et al. |
| 8,617,183 | B2 | 12/2013 | Schneider et al. |
| 9,451,944 | B2 | 9/2016 | Schneider et al. |
| 9,517,058 | B2 | 12/2016 | Harari et al. |
| 9,737,391 | B2 | 8/2017 | Harari et al. |
| 10,098,664 | B2 | 10/2018 | Harari et al. |
| 2001/0041914 | A1 | 11/2001 | Fraizer et al. |
| 2005/0234305 | A1 | 10/2005 | Licciardi |
| 2005/0250987 | A1 | 11/2005 | Ewers et al. |
| 2006/0047285 | A1 | 3/2006 | Fields |
| 2007/0239208 | A1 | 10/2007 | Crawford |
| 2008/0064962 | A1 | 3/2008 | Oonuki et al. |
| 2008/0171940 | A1 | 7/2008 | McGahan |
| 2008/0207988 | A1 | 8/2008 | Hanes |
| 2008/0208216 | A1 | 8/2008 | Cerier |
| 2009/0012557 | A1 | 1/2009 | Osypka |
| 2009/0216075 | A1 | 8/2009 | Bell et al. |
| 2010/0274074 | A1 | 10/2010 | Khamis et al. |
| 2011/0092985 | A1 | 4/2011 | Gaynor et al. |
| 2011/0092991 | A1 | 4/2011 | Gaynor et al. |
| 2011/0196389 | A1 | 8/2011 | Schneider et al. |
| 2012/0123410 | A1 | 5/2012 | Craig |
| 2014/0100580 | A1 | 4/2014 | Yu et al. |
| 2014/0324072 | A1 | 10/2014 | Harari et al. |
| 2015/0005586 | A1 | 1/2015 | Williams |
| 2015/0320442 | A1 | 11/2015 | Harari et al. |
| 2016/0235461 | A1 | 8/2016 | Sumko |
| 2017/0049548 | A1 | 2/2017 | Harari et al. |
| 2017/0196671 | A1 | 7/2017 | Harari et al. |
| 2017/0348085 | A1 | 12/2017 | Harari |

FOREIGN PATENT DOCUMENTS

| | | |
|---|---|---|
| DE | 10321012 | 12/2004 |
| JP | 2004-509685 | 4/2004 |
| JP | 2008-510589 | 4/2008 |
| JP | 2008-523926 | 7/2008 |
| JP | 2017518114 | 7/2017 |
| WO | 95/14438 | 6/1995 |
| WO | 2011/082350 | 7/2011 |
| WO | 2012/047626 | 4/2012 |
| WO | 2013/093924 | 6/2013 |
| WO | 2015/189843 | 12/2015 |
| WO | 2018/109755 | 6/2018 |

OTHER PUBLICATIONS

An International Search Report and a Written Opinion both dated Nov. 2, 2015, which issued during the prosecution of Applicant's PCT/IL2015/050585.

An International Preliminary Report on Patentability dated Dec. 15, 2016, which issued during the prosecution of Applicant's PCT/IL2015/050585.

An International Search Report and a Written Opinion both dated May 9, 2013, which issued during the prosecution of Applicant's PCT/IL2012/050548.

An International Preliminary Report on Patentability dated Oct. 21, 2014, which issued during the prosecution of Applicant's PCT/IL2012/050548.

Rofaeel, A., M.D., Peng, Philip,M.B.B.S., F.R.C.P.C., Louis, I., M.D., & Chan, Vincent, M.D., F.R.C.P.C. (2008). Feasibility of real-time ultrasound for pudendal nerve block in patients with chronic perineal pain. Regional Anesthesia and Pain Medicine, 33(2), 139-45.

An Office Action dated Apr. 8, 2016, which issued during the prosecution of U.S. Appl. No. 14/366,002.

An Office Action dated Nov. 5, 2015, which issued during the prosecution of U.S. Appl. No. 14/366,002.

Notice of Allowance dated Aug. 12, 2016, which issued during the prosecution U.S. Appl. No. 14/366,002.

Notice of Allowance dated May 12, 2017, which issued during the prosecution of U.S. Appl. No. 15/342,144.

An Office Action dated Jan. 17, 2017, which issued during the prosecution of U.S. Appl. No. 15/342,144.

U.S. Appl. No. 61/989,623. filed May 7, 2014.

Notice of Allowance dated Jun. 19, 2018, which issued during the prosecution of U.S. Appl. No. 14/667,954.

Notice of Allowance dated Jul. 10, 2018, which issued during the prosecution of U.S. Appl. No. 14/667,954.

An English translation of an Office Action dated Oct. 10, 2017 which issued during the prosecution of Japanese Patent Application No. 2016-572283.

An Office Action dated Nov. 15, 2017, which issued during the prosecution of U.S. Appl. No. 14/667,954.

U.S. Appl. No. 61/578,261, filed Dec. 21, 2011.

An English translation of an Office Action dated Dec. 19, 2017, which issued during the prosecution of Japanese Patent Application No. 2016-572283.

An Office Action dated Jun. 22, 2017, which issued during the prosecution of U.S. Appl. No. 14/667,954.

An Advisory Action dated Feb. 28, 2018, which issued during the prosecution of U.S. Appl. No. 14/667,954.

An Office Action dated Oct. 4, 2018, which issued during the prosecution of U.S. Appl. No. 15/651,472.

An English translation of an Office Action dated Aug. 23, 2018, which issued during the prosecution of Chinese Patent Application No. 201580031142.7.

An Office Action dated Jul. 10, 2017, which issued during the prosecution of Singapore Patent Application No. 11201610287V.

European Search Report dated Dec. 11, 2017 which issued during the prosecution of Applicant's European App No. 15806208.3.

An Office Action dated Jan. 7, 2020, which issued during the prosecution of U.S. Appl. No. 15/316,698.

SYSTEM AND METHOD FOR PELVIC FLOOR PROCEDURES

RELATED APPLICATION

The present application is a continuation application of U.S. patent application Ser. No. 14/667,954, filed Mar. 25, 2015, entitled SYSTEM AND METHOD FOR PELVIC FLOOR PROCEDURES, which claims the benefit of priority under 35 USC 119(e) of U.S. Provisional Patent Application No. 61/989,623 filed on May 7, 2014, the contents of both of which are incorporated herein by reference in their entirety.

FIELD AND BACKGROUND OF THE INVENTION

The present invention relates to a system and method for rapid, safe and accurate access to pelvic floor tissues with minimal tissue trauma. Embodiments of the present invention relate to a system capable of guiding and anchoring a tissue repair device and/or implant in treatment in pelvic floor tissue.

Trans-vaginal pelvic floor repair is a surgical procedure which utilizes blunt tissue dissection to provide access to the sacrospinous ligament from the posterior vaginal wall. A sling or mesh is then anchored to the sacrospinous ligament and the vaginal apex or the uterine isthmical fibrotic ring, cervix or body, to thereby support prolapsing tissues and/or organs.

Although pelvic floor repair is a common procedure, access to the sacrospinous ligament is typically effected by improvised manual blunt dissection techniques and/or use of off the shelf instruments.

Centro-apical reconstruction is the key for proper pelvic organ prolapse (POP) repair. The premium supportive pelvic structure is the sacrospinous ligament (SSL) which is positioned at the posterior aspect of the pelvis. The SSL is a robust ligament and thus provides a long lasting solution. Since it is positioned high in the pelvis and medially the SSL provides a level 1 support (DeLancey) and reduces the likelihood of dyspareunia when utilized for prolapse repair.

Vaginal wall access to the SSL can be difficult and hazardous since organs and tissues surrounding the access path can easily be injured during dissection. Present day approach for accessing the SSL starts with an incision at the mid-line of the posterior or anterior vaginal wall followed by lateral dissection under the sub-mucosal fascia to the pelvic side wall and dissection towards the ischial spine to the mid SSL (MSSL).

This approach decreases risk of tissue injury by bypassing the bladder/rectum while maintaining accurate navigation along the above mentioned landmarks. Such an approach requires a high degree of skill and as such can lead to a high rate of complications; this prompted the FDA to issue a significant risk warning associated with POP reconstruction.

While reducing the present invention to practice, the present inventors have devised a system and method which can be used to deliver a tissue anchor to anatomical landmarks and structures such as the ischial spine and the sacrospinous ligament from the vaginal cavity.

SUMMARY OF THE INVENTION

According to one aspect of the present invention there is provided a device for tissue anchor delivery comprising: (a) a first flexible tube having a rigid distal portion attachable to a tissue anchor; (b) a second flexible tube coaxially disposed around the first tube; and (c) a tubular sheath covering the second flexible tube.

According to further features in preferred embodiments of the invention described below, the first flexible tube is constructed from a spirally wound wire.

According to still further features in the described preferred embodiments the second flexible tube is constructed from a spirally wound wire.

According to still further features in the described preferred embodiments the device further comprises the tissue anchor.

According to still further features in the described preferred embodiments the tissue anchor is attached to the rigid distal portion and disposed within the second flexible tube.

According to still further features in the described preferred embodiments the first flexible tube can be advanced within the second flexible tube when the first and the second flexible tubes are constrained along a non-linear path.

According to still further features in the described preferred embodiments the second flexible tube can be advanced within the tubular sheath.

According to still further features in the described preferred embodiments advancing the first flexible tube within the second flexible tube ejects the tissue anchor from the flexible tube.

According to still further features in the described preferred embodiments the tissue anchor is configured such that a portion thereof increases in diameter when ejected from the second flexible tube.

According to another aspect of the present invention there is provided a system for delivering an anchor to tissue comprising: (a) a housing adapted for attachment to an ultrasound probe, the housing including at least one guide disposed thereupon; (b) a device for tissue anchor delivery including: (i) a first flexible tube having a rigid distal portion attachable to a tissue anchor; (ii) a second flexible tube coaxially disposed around the first tube; and (iii) a tubular sheath covering the second flexible tube; the device being attachable to the at least one guide such that when the housing is attached to the ultrasound probe, the rigid distal portion can be longitudinally aligned with an image plane of the ultrasound probe.

The present invention successfully addresses the shortcomings of the presently known configurations by providing a transvaginal or trans-rectal/anal anchor delivery system which enables accurate delivery and anchoring of an attached suture or mesh to an anatomical landmark in the pelvic floor while minimizing trauma and eliminating risk to surrounding tissue and organs.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
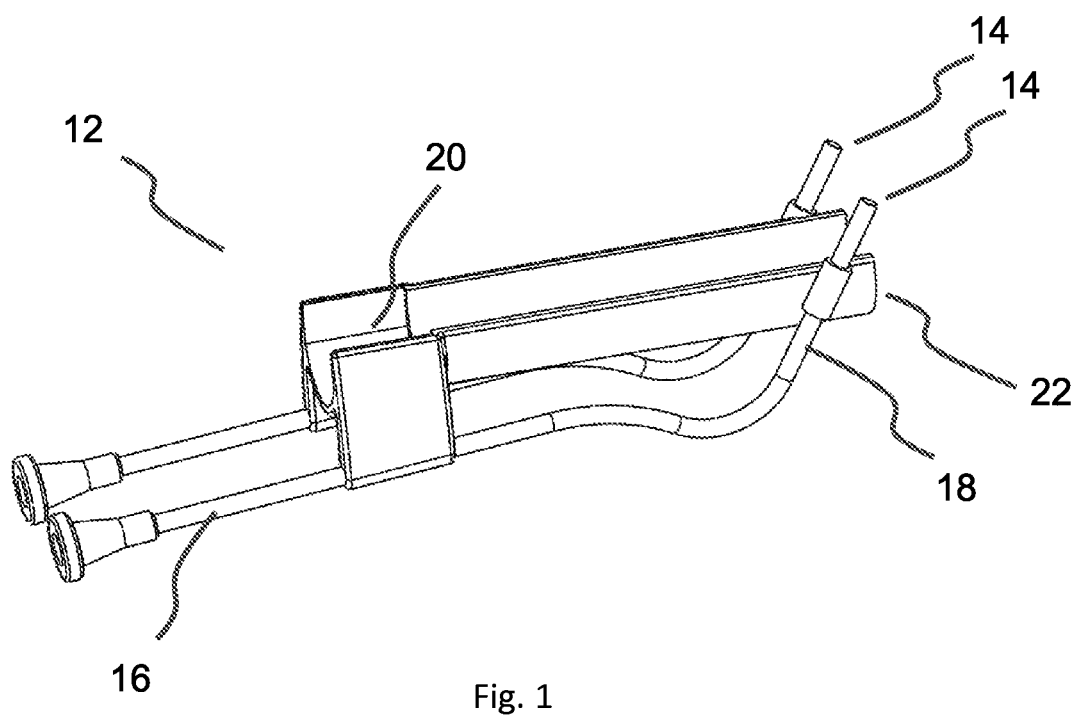
FIG. 1 illustrates one embodiment of the imaging device coupler having two guide tubes, one loaded with an anchor delivery device.
Figure 2A:
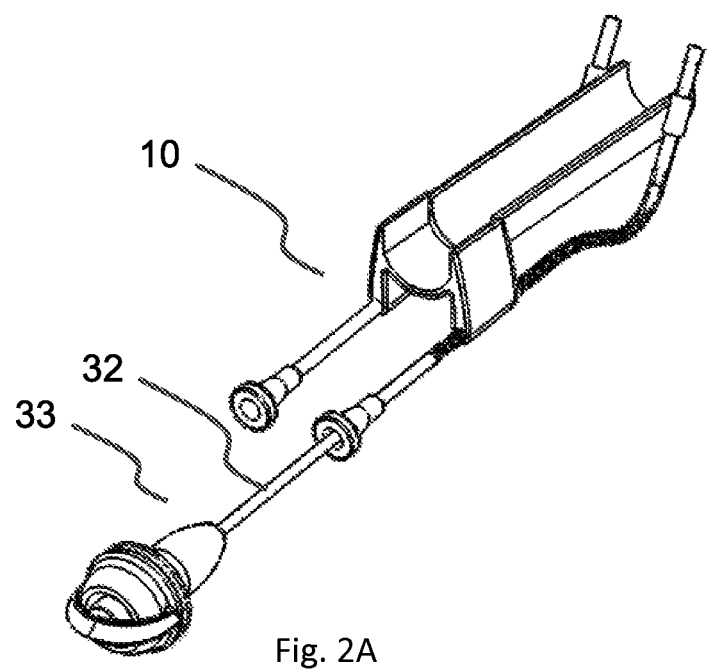
FIGS. 2A-B are views of the device coupler of FIG. 1, showing the distal tip of the anchor delivery device extending out of the guide tube (FIG. 2A), and the anchor extending out of the distal tip of the guide tube (FIG. 2B).
Figure 2B:
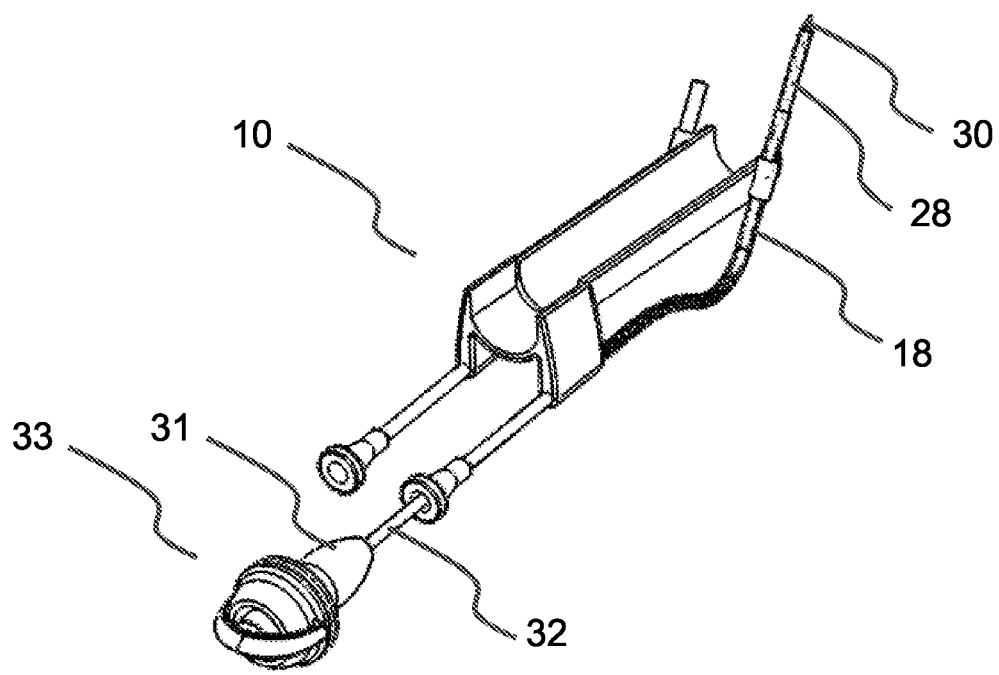

The present invention is of a system and method which can be used to deliver tissue anchors and optionally anchor-attached devices (e.g. sling/mesh) to anatomical landmarks in the pelvic floor in order to repair pelvic floor disorders such as pelvic organ prolapse (POP).

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description, Example or drawings. The invention is capable of other embodiments or of being practiced or carried out in various ways. Also, it is to be understood that the phraseology and terminology employed herein is for the purpose of description and should not be regarded as limiting.

Pelvic organ prolapse (POP), and especially apical central supportive defect (ACSD), significantly affects the quality of life of about 20% of the female population. POP is typically corrected via a transabdominal or a transvaginal surgical procedure.

The transvaginal reconstruction approach is regarded as superior to the transabdominal approach due to a shorter operative time and hospital stay and quicker rehabilitation. However, transvaginal procedures require advanced surgical skill and as such are performed by a rather small and highly qualified group of surgeons.

In the transvaginal procedure, a surgeon can elect to suspend the vaginal apex (VA) or the uterine cervix (UC) to the sacrospinous-ligament (SSL), sacrum, arcus tendineous fascia pelvis (ATFP) or other potentially solid supportive pelvic structures, which are accessed via anterior or posterior vaginal wall incisions and blunt dissection of tissues.

Creating an access path to these tissues is a major challenge of transvaginal procedures since it requires complicated navigation to the pelvic side wall (PSW), ischial spine (IS) and then to the mid SSL (MSSL) or the sacrum which carries with it a risk of damaging the bladder, rectum, blood vessels, nerves, ureters, etc.

Most POP procedure complications are attributed to the dissection necessary to create the tissue path to the elected tissue support site.

In order to traverse these limitation of prior art transvaginal procedures, the present inventors have devised a system which is capable of accessing anatomical landmarks within the pelvic floor and accurately delivering a tissue anchor thereto while minimizing tissue trauma and complications.

As used herein, the phrase "pelvic floor disorder" refers to any disorder of the pelvic floor that is associated with prolapse, herniation or incorrect anatomical positioning of pelvic floor tissues.

The term "repair" when used herein with reference to pelvic floor disorders refers to correction (complete or incomplete) of anatomy, via, a tissue repair device such as a suture, a mesh, a sling and/or the like. An example of a repair procedure effected using the present methodology and system is described below.

Thus according to one aspect of the present invention there is provided a system for delivering a device such as an anchor (attached to a suture or mesh) to a tissue.

The system includes a housing (also referred to herein as coupler) adapted for attachment to an imaging probe, such as an ultrasound probe. The coupler includes at least one guide disposed thereupon for accepting a device for tissue anchor delivery (also referred to herein as delivery device or anchor delivery device).

The guide(s) are constructed from a rigid tube.

The coupler and guide are configured such that when the coupler is attached to the imaging probe, the rigid distal portion of the delivery device can be longitudinally aligned with an image plane of the imaging probe.

The imaging device can be any type of imaging device suitable for tissue imaging from within the rectal or vaginal cavity. Examples of suitable imaging devices include infrared imaging devices and the like. Such devices are configured so as to enable insertion into, and use within the cavity of choice.

In a preferred embodiment of the present system, the imaging probe is an ultrasound transducer with an imaging plane that projects at an angle (e.g. 45-90 degrees) with respect to the longitudinal axis of the probe. The coupler and attached guide(s) are configured so as to enable the distal tip of the delivery device to align with the imaging plane of the probe such that an anchor is delivered parallel to and within the imaging plane of the probe, i.e. it is delivered into an imaged tissue plane.

FIGS. 1-4 illustrate one embodiment of the present system which is referred to herein as system 10.

FIG. 1 illustrates coupler 12 having two delivery guides 14 configured as tube-like channels. In this embodiment of coupler 12, delivery guides 14 include proximal guide tube portion 16 and distal guide tube 18 portion.

Coupler 12 can include any number of guides 14, the embodiment of FIGS. 1-4 are of a coupler 12 that includes two side mounted guides 14 that enable anchor delivery from either or both sides of coupler 12.

Coupler 12 is roughly trough-shaped (with open proximal and distal ends) and is constructed from a polymer such as ABS or Polycarbonate with a length of 80-120 mm, width of 25 and a height of 20-30 mm. Coupler 12 can include a handle for delivery into a cavity, or alternatively, a handle of an attached imaging device can be used for such purposes.

Coupler 12 includes a probe coupling interface 20 for accepting and reversibly attaching to an imaging probe such as an ultrasound probe. In one embodiment of coupler 12, the imaging probe snaps into interface 20 and is longitudinally aligned therewith with the imaging head occupying a predetermined longitudinal position at distal end 22 of coupler 12. This ensures that the imaging head of the imaging probe and its projected image plane are a known distance (longitudinally) from distal guide tube 18.

System 10 also includes an anchor delivery device 33 which is constructed from two coaxial tubes. A first flexible tube 32 (shown in FIGS. 2A-B) attached to a tissue anchor 30 (shown in FIG. 2B). A rigid guide 14 is coaxially disposed around anchor delivery device 33. The tubes of anchor delivery device 33 can be pushed out of rigid guide 14 to deliver tissue anchor 30 via rigid distal portion 18 of guide tube 14. To effect such delivery, delivery device includes a handle 31 for actuating forward movement (in a distal direction) of first flexible tube 32 within guide tube 14.

Delivery device 33 is preferably capable of puncturing the vaginal wall and driving tissue anchor 30 through the tissue and into the target site. As such, distal end 28 of first flexible tube 32 can be configured for tissue puncturing (beveled, double beveled or conical). Alternatively, tissue anchor 30 can be configured for tissue puncturing or still alternatively an initial incision in the vaginal wall can be used to deliver first flexible tube 32 therethrough. Distal portion 28 (and/or anchor 30) can also include an imaging marker for identifying these elements within the imaging plane. An example of an echogenic marker which can be used along with an ultrasound probe is provided in US20050228288. Delivery device 33 is described in more detail hereinbelow with reference to FIGS. 5A-D, while anchor 30 is described in more detail hereinbelow with reference to FIGS. 6A-F.

Figure 3:
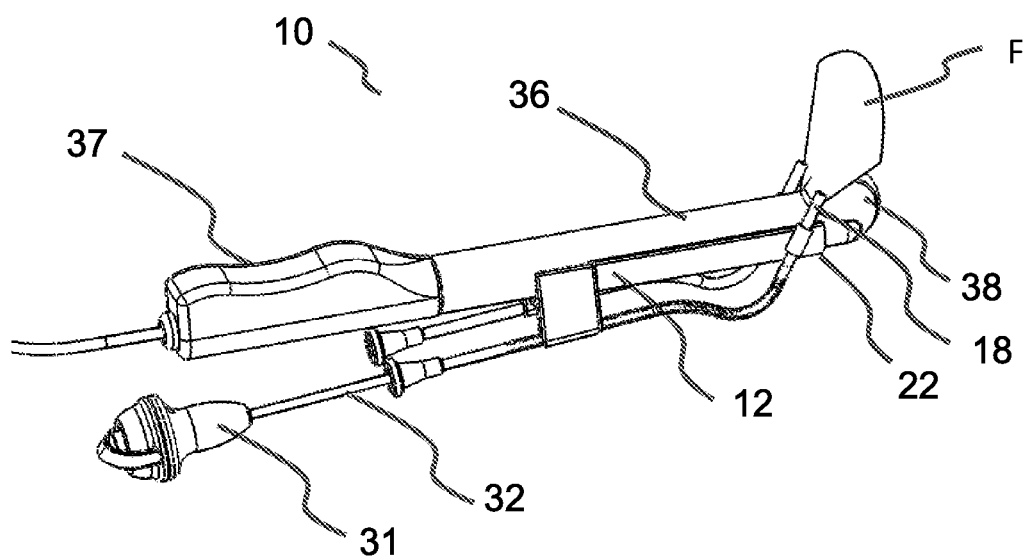
FIG. 3 illustrates the imaging device coupler of FIG. 1 mounted on an ultrasound transducer showing the alignment between the imaging field of the transducer (F) and the path of the guide tubes.

FIG. 3 illustrates coupler 12 attached to an imaging probe 36 (vaginal/anal ultrasound probe illustrated) with imaging head 38 protruding from a distal end 22 of coupler 12. Imaging field (plane) of imaging head 38 is indicated by F and is about 70 degrees (forward tilt) with respect to the longitudinal axis of imaging probe 36.

The angle of distal guide tube portions 18 can either be fixed to the type of probe 36 used or it can be manually adjusted (by rotating) and locked in a rotational position suitable for the imaging plane of the imaging probe used.

Figure 4:
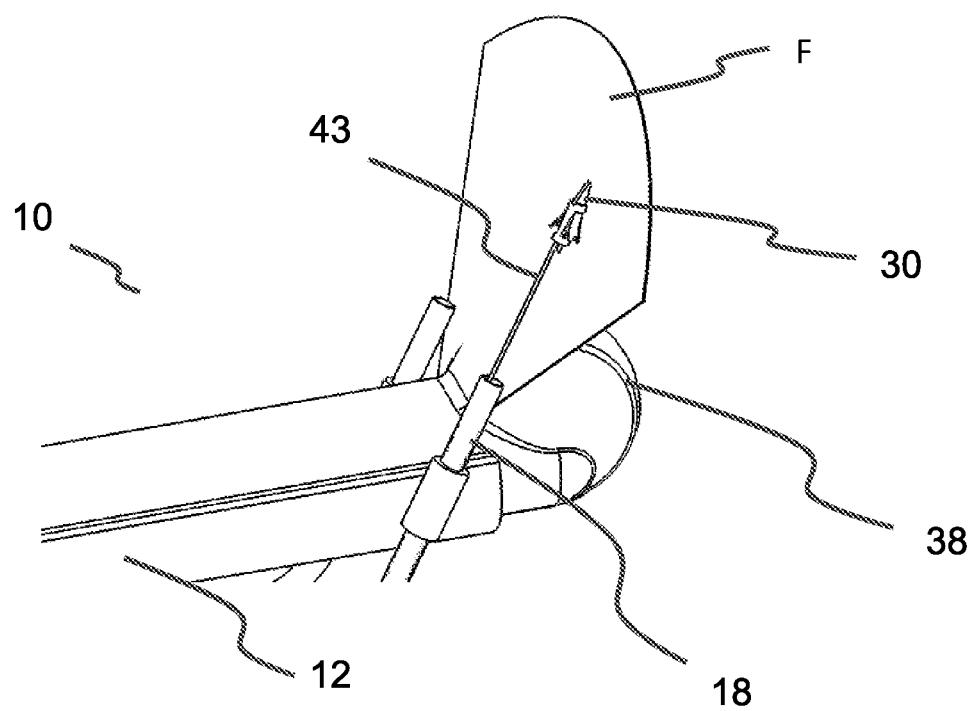
FIG. 4 illustrates the imaging device coupler of FIG. 1 mounted on an ultrasound transducer showing the alignment between the imaging field of the transducer (F) and the delivery path of the anchor.

In any case, the angle of distal guide tube portions 18 is aligned with the imaging plane (F) such that distal portion 28 delivers an anchor 30 into and parallel with imaging plane F. Plane (F) is thinner than distal portion 28 (2.5 mm) such that distal portion 28 is always visible on screen. FIG. 4 illustrates an anchor 30 with an attached suture 43 delivered into the imaging plane (and thus the tissue viewed therein), distal portion 28 of first tube 32 is not shown.

Figure 5A:
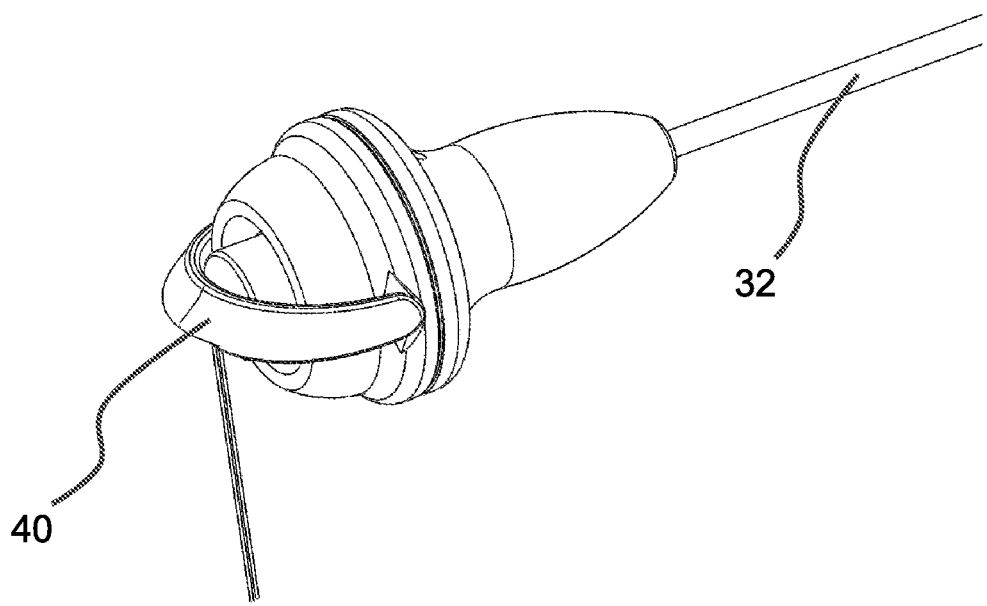
FIGS. 5A-D illustrate the anchor delivery device of the present invention, showing the handle and tube assembly in non-deployed (FIGS. 5A-B) and deployed (FIGS. 5C-D) states.
Figure 5B:
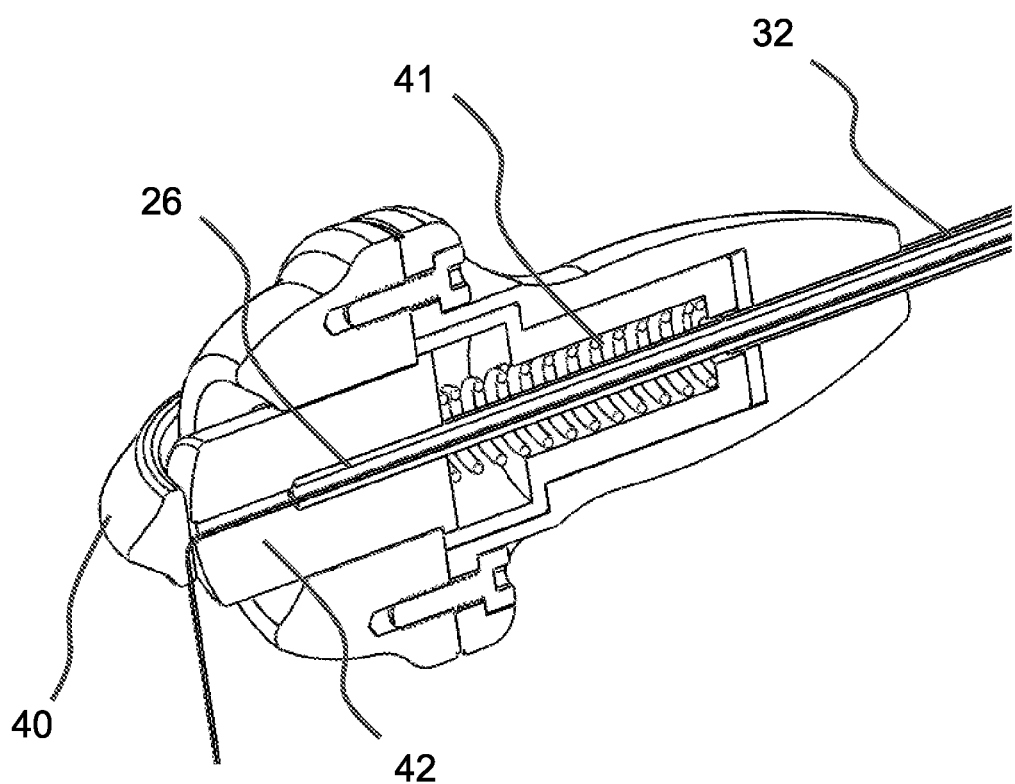
Figure 5C:
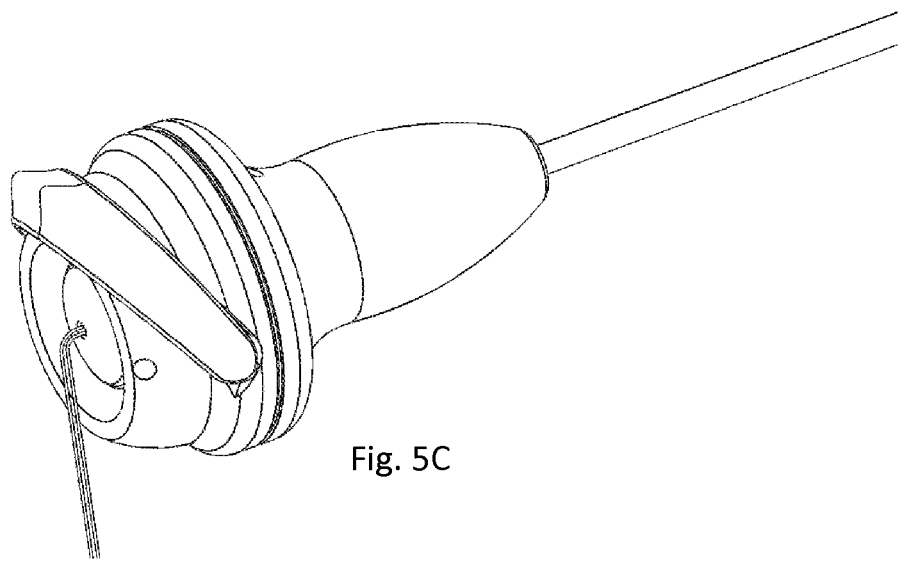
Figure 5D:
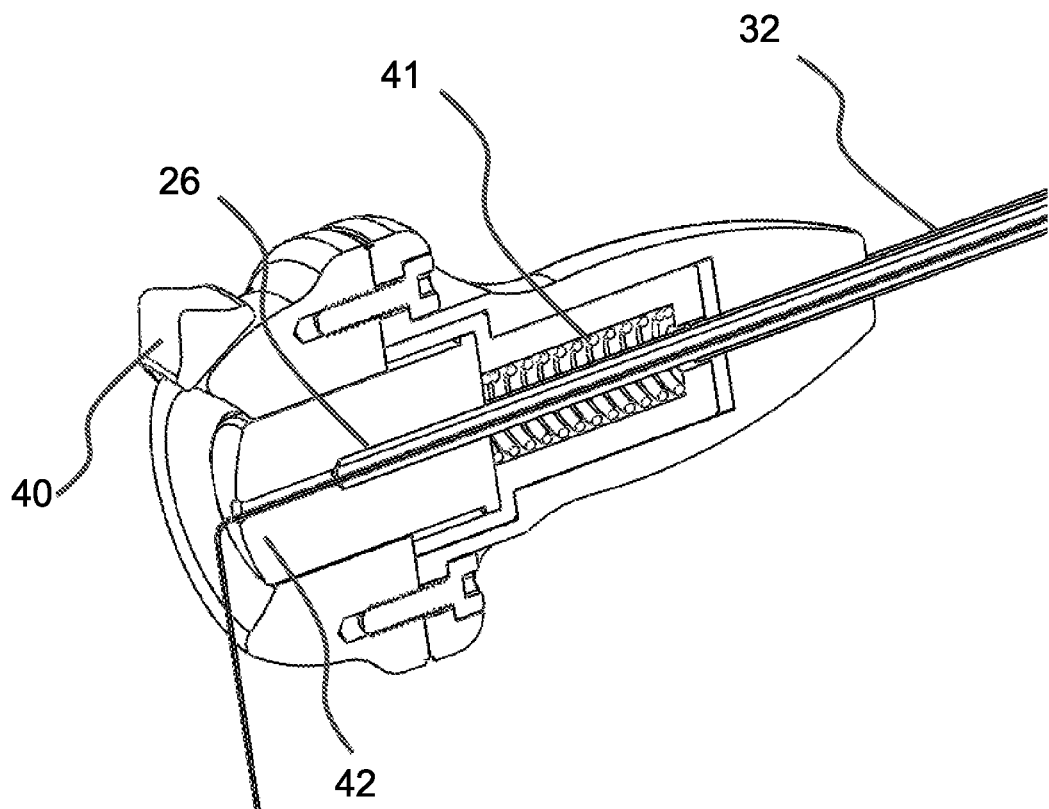

FIGS. 5A-B illustrate handle 31 in its idle (pre-deployed) position. Trigger 40 protects button 42 from being pressed prematurely. Button 42 is connected to first flexible tube 26. Button 42 is held in its idle position by force applied by spring 41. FIGS. 5C-D illustrate handle 31 in the deployed position. Rotation of trigger 40 enables an operator to access button 42, which when pressed, actuates first flexible tube 26 to deploy (push out) anchor 30.

Flexible portion of tubes 26 and 32 can be made from a flexible polymer or a preloaded spring.

Figure 6A:
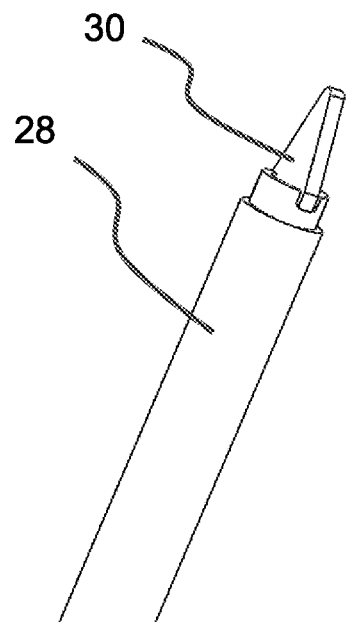
FIGS. 6A-F illustrate one embodiment of a tissue anchor constructed in accordance with the teachings of the present invention.
Figure 6B:
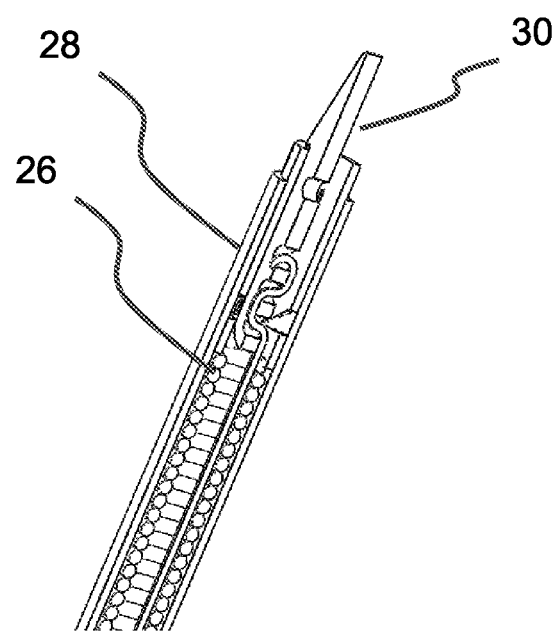

FIGS. 6A-B illustrate anchor 30 constrained by distal portion 28 of tube 32.

Figure 6C:
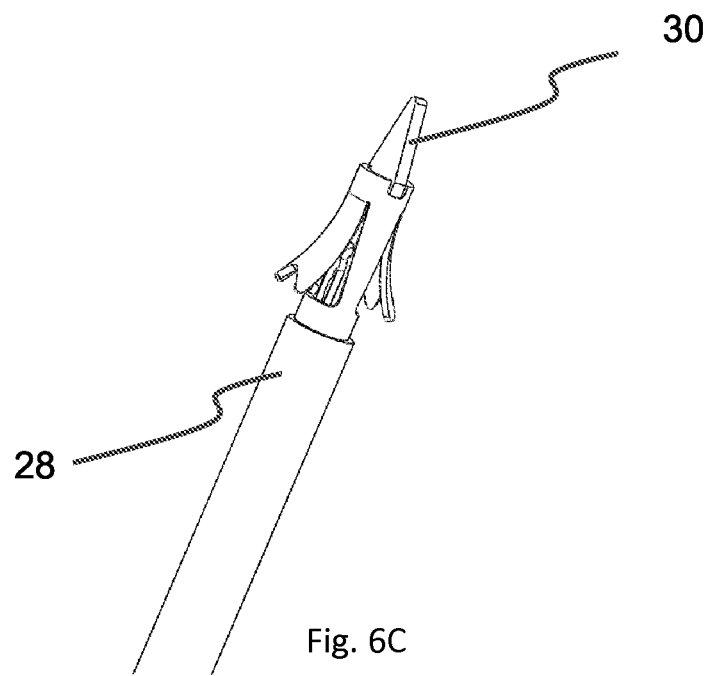
Figure 6D:
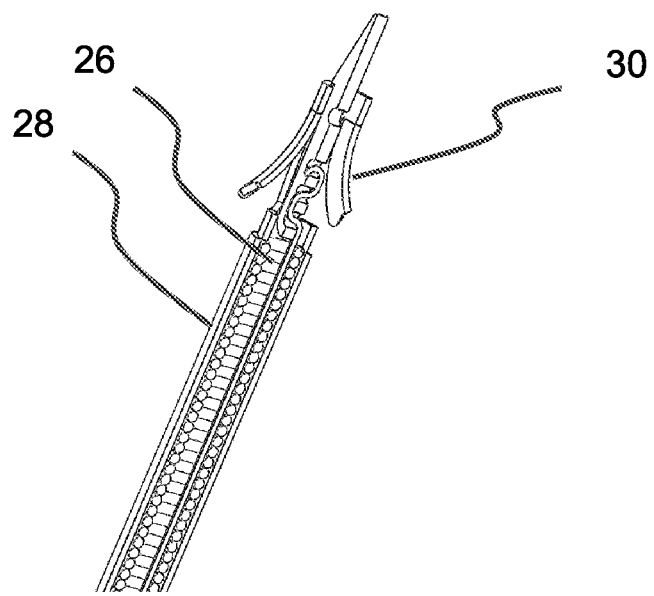
Figure 6E:
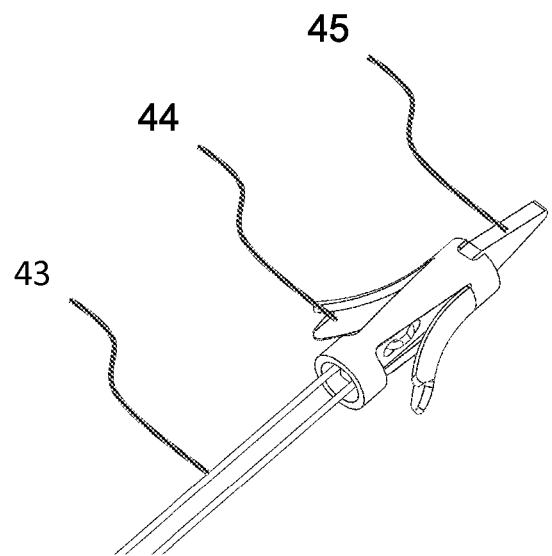

Anchor 30 is in contact with flexible portion of tube 26. FIGS. 6C-D illustrate anchor 30 in its unconstrained position after being pushed out of distal portion 28 of tube 32. Anchor 30 is shown in its unconstrained position. FIG. 6E illustrates anchor tube 44 and anchor tip 45 of anchor 30 and attached suture 43.

Figure 6F:
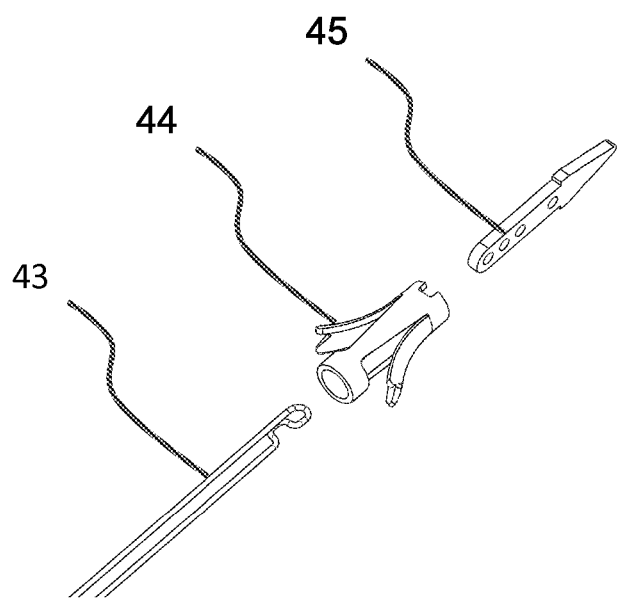

FIG. 6F illustrates anchor 30 in its unassembled state. Anchor tube 44 and anchor tip 45 are composed of nitinol or a polymer such as PEEK. They can be laser welded together or alternatively connected mechanically via a snap. Suture 43 is composed of prolene or any surgical suture material. Anchor 30 can be 2 mm in diameter and 8 mm in length. Anchor 30 can be configured with a pull out force of about 30N.

One preferred use for system 10 is in centro-apical reconstruction procedures.

Such procedures are the key to proper pelvic organ prolapse (POP) repair. The premium supportive pelvic structure is the sacrospinous ligament (SSL), positioned at the posterior aspect of the pelvis. The SSL is high, thus provides a level 1 support by DeLancey. The SSL is a stable anatomical landmark and as such it is highly suitable for anchoring support.

System 10 can be used in centro-apical reconstruction procedures by positioning coupler 12 with attached probe 36 in a rectal, anal or vaginal cavity (using handle 37 of probe 36 or a handle incorporated into coupler 12), inserting delivery device 33 through guides 14, and advancing distal portion 28 of delivery device 33 (with attached anchor 30) through a vaginal wall under guidance of an ultrasound probe to thereby reach a target tissue within the pelvic floor (e.g. SSL). Once at the target tissue, anchor 30 can be deployed into the target tissue by advancing first flexible tube 26 within second flexible tube 32 using handle 31.

Imaging enables direct visualization of the MSSL and alignment between the imaging plane and distal portion 28 of delivery device 33 enables accurate navigation of anchor 30 thereto providing a surgeon with transvaginal access to the MSSL through the lateral vaginal wall and minimizing risks associated with posterior or anterior access (injury to the rectum or bladder).

A transvaginal pelvic organ prolapse (POP) repair procedure using system 10 described in greater detail below.

An ultrasound probe is coupled to coupler 12 and an anchor 30 is loaded into system 10. System 10 is positioned in the vaginal cavity and secured to the uterine cervix. The US probe is activated and the posterior compartment of the pelvic floor is scanned, to locate the SSL. Color Doppler is activated to rule out any blood vessel on the imaginary target of the anchoring needle, towards the MSSL (or any other ligament segment). Anchor 30 is deployed as described above on one lateral vaginal fornix, and initial pull out force is measured to verify fixation. This is optionally repeated on the other side. System 10 is removed from the vaginal cavity and the free sutures entering the vagina are needle passed back beyond the vaginal wall and sutured to the cervical fibrotic ring, via a small colpotomy.

The present coupler and delivery device (the present system) can be used to perform transvaginal pelvic floor procedures with ease and while minimizing tissue damage and trauma. The present system is advantageous in that:

(i) it does not require posterior or anterior vaginal dissections which can jeopardize the rectum or bladder;

(ii) it enables direct visualization of the target tissue (e.g. MSSL) for accurate navigation of a minimally invasive surgical instrument;

(iii) US provides a clear image of the surgical instrument tip at the target tissue (e.g. MSSL), since the imaging plane and anchor are aligned;

(iv) it minimizes unwanted damage to visceral and vessel tissue during the procedure; and (v) it eliminates the need for deep pelvic manual dissection and Hydrodissection.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following example, which together with the above descriptions, illustrate the invention in a non limiting fashion.

SSL Imaging

Figure 7:
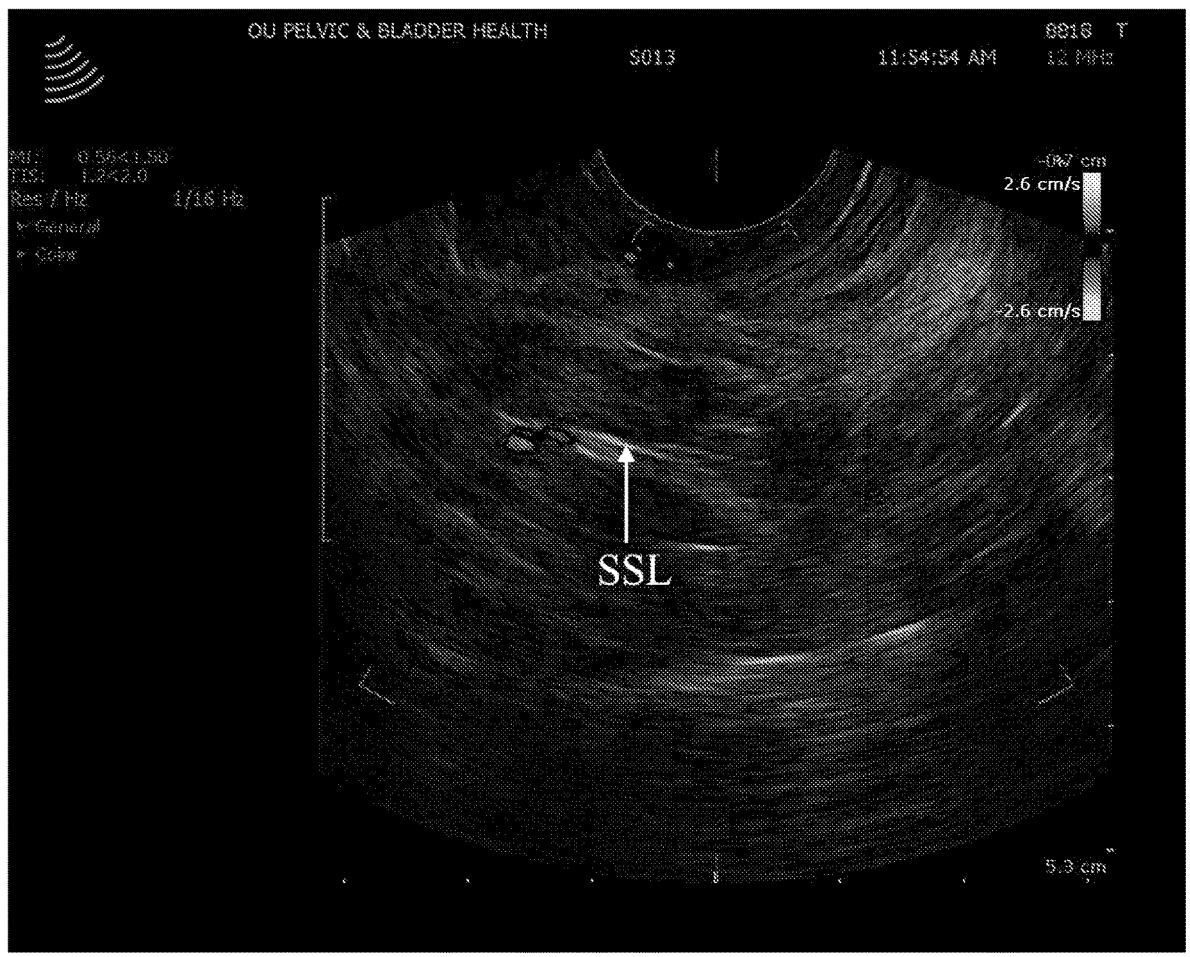
FIG. 7 is an ultrasound image showing the SSL.

An angled vaginal ultrasound (Side Fire) probe was utilized in order to visualize the SSL. As is shown in FIG. 7, the MSSL is easily demonstrated (arrow) with angled US probe as it is attached to the sacrum at its mid-level and goes laterally. The tissue surrounding the SSL is the piriformis muscle, also easily detected via angled ultrasound imaging.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A system for attaching an anchor to a ligament located outside of a vaginal wall, the system comprising:
    a vaginally insertable assembly extending along a longitudinal axis, said vaginally insertable assembly having an open proximal end and an open distal end;
    a working channel fixed to said vaginally insertable assembly and extending along at least an elongate portion thereof at an angle with respect to said longitudinal axis, said working channel having a distal end, which is fixed with respect to the vaginally insertable assembly at a first location on said vaginally insertable assembly, and a proximal end, which is rearward of said open proximal end of said vaginally insertable mounting assembly, said working channel also being fixed to said vaginally insertable assembly at a second location on said vaginally insertable assembly, rearward of said first location; and
    a suture and penetrating anchor assembly which is configured to be displaceable at least along said elongate portion of said working channel through said vaginal wall and into anchoring relationship with said ligament.

2. A system according to claim 1 and wherein said suture and penetrating anchor assembly comprises a laterally expandable anchor.

3. A system according to claim 1 and wherein said suture and penetrating anchor assembly is configured to remain at said angle with respect to said longitudinal axis when displaced through said vaginal wall into said anchoring relationship with said ligament.

\* \* \* \* \*